(12) United States Patent
Deymes et al.

(10) Patent No.: US 8,216,616 B2
(45) Date of Patent: Jul. 10, 2012

(54) SALIVARY SUBSTITUTE

(75) Inventors: Jean Deymes, Bordeaux (FR); Philippe Perovitch, Le Temple (FR)

(73) Assignee: Unither Developpement, Amiens (FR)

( * ) Notice: Subject to any disclaimer, the term of this patent is extended or adjusted under 35 U.S.C. 154(b) by 502 days.

(21) Appl. No.: 12/439,362

(22) PCT Filed: Aug. 28, 2007

(86) PCT No.: PCT/FR2007/051850
§ 371 (c)(1),
(2), (4) Date: Feb. 27, 2009

(87) PCT Pub. No.: WO2008/025926
PCT Pub. Date: Mar. 6, 2008

(65) Prior Publication Data
US 2009/0317484 A1  Dec. 24, 2009

(30) Foreign Application Priority Data

Sep. 1, 2006  (FR) ...................................... 06 53549

(51) Int. Cl.
*A01N 65/00* (2009.01)
(52) U.S. Cl. ...................................................... 424/725
(58) Field of Classification Search ........................ None
See application file for complete search history.

(56) References Cited

U.S. PATENT DOCUMENTS
2005/0226822 A1  10/2005  Garbers et al.

FOREIGN PATENT DOCUMENTS
WO  99/04804  2/1999

OTHER PUBLICATIONS

Answers .com, 1 page, 2011.*
Wolinsky L et al.: "The inhibiting effect of aqueous Azadirachta indica (neem) extract upon bacterial properties influencing in vitro plaque formation" Journal of Dental Research, vol. 75, No. 2, 1996, pp. 816-822, XP002426645.
International Search Report issued on Feb. 15, 2008, Application No. PCT/FR2007/051850.

\* cited by examiner

*Primary Examiner* — Michael Meller
(74) *Attorney, Agent, or Firm* — Young & Thompson

(57) ABSTRACT

A salivary substitute is produced from egg white so as to have chemical, rheological and physiological properties that are analogous to those of natural human saliva. A packaging containing the salivary substitute and uses of the salivary substitute are also disclosed.

5 Claims, No Drawings

SALIVARY SUBSTITUTE

This invention relates to a substitute for the natural saliva that is produced from egg white.

The invention also relates to its uses and its packaging.

Salivary deficiency or xerostomy is a very common pathology that leads to significant undesirable effects at the level of the buccopharyngeal sphere. Its origins are many: immune ailments, secondary effects of numerous medications, age, menopause or else treatments of buccopharyngeal cancers by radiotherapy. It brings about a buccal dryness that can have serious consequences that range from problems of phonation to anorexia, with psycho-depressive effects.

These extremely uncomfortable problems that are caused by xerostomies are well known, but there is currently no satisfactory treatment that makes it possible to rebalance the buccal atmosphere.

A solution for fighting against the buccal dryness produced by salivary deficiency is to administer reconstituted saliva.

Saliva is a biological liquid that moistens the mucous membranes of the mouth and the pharynx, and facilitates phonation, mastication, and swallowing. It also performs an antiseptic function and has a role in protecting the esophagus.

The saliva is a very specific and composite medium that is complex and consists for the most part of water. This medium is both a reflection of the plasmatic composition and carrier of substances that are synthesized by the exocrine salivary glands, in particular proteins of high molecular weight, including mucins, globulins, glucoproteins, enzymes, minerals, and compounds that intervene in anti-infectious protection. Its balanced and multifunctional composition is difficult to reconstitute reliably and in a stable manner, taking into account delicate and subtle interactions that take place continuously between its different components.

There are a certain number of products that attempt to replace the effect of saliva.

For example, a product that is based on mineral salts, sorbitol and water is known.

It is also possible to cite a gel that primarily contains polymer substances of extractive or synthetic origin, polyols and enzymes whose stability is uncertain in these surroundings.

Other preparations come in the form of synthetic active ingredients, including in particular one based on polyethylene oxide.

There is also a product that consists of oxidized glycerol triesters (Aequasyal®) that, applied on mucous membranes that are already dried out and inflamed, forms a lipid film that is not conducive to constituting an active substrate that will promote biological exchanges.

Finally, mucins that are extracted from a porcine stomach have been used combined with minerals and polyols to attempt to reproduce the effect of salivary mucins. All of these products are extremely far removed from Theological complexity, the muco-protective effect and the biological activity of natural saliva. They have a different composition and different behaviors, which prevent them from providing even close to as complex an equivalent functionality and from participating in buccal homeostasis.

Patent applications and patents that deal with this subject are also known.

Thus, the U.S. patent application US 2005/0226822 describes a substitute for human saliva that comprises the ovomucin that is obtained from egg white. This application exclusively provides this use of a compound of egg white, then excluding the other components of the complete egg white.

The international patent application WO 99/04804 relates to the use of immune secretions, starting from milk or an egg, obtained from animals to which pathogenic elements have been administered. This document aims at applications that include as much xerostomy as tooth decay or buccal inflammations. Obtaining such compositions is complex and requires the installation of a chain that includes the animals themselves.

There is therefore a need for reconstituted saliva with a composition and qualities that are analogous to natural saliva, with means for industrial implementation and production.

This is why the objective of this invention is to propose a salivary substitute that is based on an easily available biological medium that mimics the composition and intricate balances of saliva.

For this purpose, the invention aims at a salivary substitute that is obtained from egg white.

This substitute has chemical, Theological and physiological properties that are analogous to those of natural human saliva.

Advantageously, the egg white is a natural protein compound that assembles almost all of the components of saliva, in an equivalent balance. It also has a similar covering power and an analogous viscosity, allowing various components to coexist among them.

According to another advantage of the invention, the egg white is a naturally aseptic medium whose composition stability is well known.

The invention is now described in detail according to particular non-limiting embodiments, with an illustration by a packaging in a particular container.

The salivary substitute according to the invention comprises at least one egg white.

The egg white consists of a set of elements of organic origin, similar to those of the physiological human saliva that makes it particularly suitable for the production of a salivary substitute that is close to natural saliva.

Egg white is a stable product.

Natural saliva consists of proteins of high molecular weight that provide its viscosity, its covering power of the mucous membranes and teeth at the same time that they ensure the exchanges and attachments of minerals on dental enamel. These proteins are primarily mucins and immunoglobulins A, and acidic glycoproteins.

The proteins of egg white are analogous in terms of nature, molecular weight and structure to the constituent proteins of saliva. It is possible to cite in particular:

Ovalbumin, which represents 54% of proteins with very large molecular structure, Ovotransferrin, present at 12-13%, which attaches the iron atoms, blocking the bacterial reproduction, Ovomucoid, present at 11%, protease inhibitor, Ovoglobulins G2, G3, ovoflavoproteins, ovoinhibitors, with a molecular weight of 50 KDa, present at about 5%, Ovomucin, present at 3.5%, mucin with a very large molecular weight (between 210 and 720 KDa) that interacts with ovalbumin, ovotransferrin and lysozyme, and Ovomacroglobulin of very high molecular weight (between 760 and 900 KDa) for 0.5%.

The egg white also contains a particular enzyme of the saliva, the lysozyme.

Regarding the mineral contributions of egg white, in particular the Na/K ratio, they are completely suitable for the needs of natural saliva. In addition, the contributions of calcium, phosphorus, magnesium, sulfur and chlorine meet the requirements of mineralization of the buccodental space.

According to one embodiment of the invention, it is possible to add to the egg white substances that will increase its capability of moistening, biological protection of mucous membranes and teeth, physico-chemical exchanges, softening of inflamed tissues and rebalancing of acidic pH of the tissues to a neutral pH.

In particular, it is possible to add substances that make it possible to regulate the viscosity of the salivary substitute. Actually, natural saliva foams and loads itself spontaneously with air in the buccal cavity, forming a mixed phase of air and water that are connected by surface-active phenomena.

Thus, the salivary substitute that is based on egg white according to the invention can comprise at least one substance that allows the adjustment of the viscosity between 1 and 5 poise, for coming close to that of a healthy mouth of between 1.25 and 1.35 poise, and that produce a surface tension of between 16 and 22 dyne/cm$^{-1}$. This substance is preferably selected from among:

Cellulose Derivatives:
- sodium carboxymethyl cellulose
- hydroxyethyl cellulose
- hydroxypropyl cellulose
- hydroxypropyl methyl cellulose or hypromellose
- carboxymethyl cellulose Gums:
- guar
- xanthan
- gum arabic Non-Cellulose Polymers:
- alginic acid and derivatives
- carboxy-vinyl polymers
- carbomers
- polyethylene glycol
- gelatin
- povidone
- pectins It is also possible to select other polymer structures such as hyaluronic acid or polyols, such as sorbitol or mannitol.

To meet the requirements of a suitable salivary substitute, it is also important to adjust the pH—for the purpose of restoring a neutral pH, and even ideally close to 7—to the buccal atmosphere in these pathologically acidic mouths. Actually, the slightly alkaline pH of the substitute, preferably between 7.5 and 9, makes it possible to protect the stability of certain substances of natural origin, such as lysozyme, and makes it possible to buffer the buccal pH to a physiological level.

Thus, the salivary substitute that is based on egg white according to the invention can also comprise at least one substance that allows the adjustment of the pH between 7.5 and 9, preferably by composition of a buffer effect based on sodium bicarbonate and calcium carbonate or calcium orthophosphate.

It is optionally possible to combine with these elements specific supplements, intended in particular to compensate for the particular deficits linked to xerostomies, namely in particular:

- sialic acid or N-acetyl-neuraminic acid, already present in the majority of egg-white proteins,
- hyaluronic acid, a molecule that is extensively used in all of the tissues of the organism, able to play a hydration-sensor and mucoprotective role to soften and protect the buccal atmosphere,
- lactoferrin, to increase the defense capacity of the medium against bacteria, viruses and mycosic agents,
- polyols, in particular sorbitol or mannitol for their moisture-retention aspect,
- sodium fluoride or calcium fluoride that inhibits by simple contact the formation of cariogenic acids in these xerostomic mouths, in particular dosed at 0.5/1 mg/l,
- natural extracts, in particular a Neem extract that acts on the glucans and bacteria that constitute dental plaque, and/or
- an extract of green tea, rich in decay-reducing fluorine, and halitosis-reducing polyphenols, which also participates in preventing gingivitis and bacterial proliferation.

It is also possible to add lysozyme, although egg white already contains it in a sufficient quantity to compensate for possible losses.

The salivary substitute according to the invention has a composition that is analogous to that of a physiological natural saliva. It can advantageously be used to provide elements that are indispensable to calming and reestablishing homeostasis in dried-out mouths.

The reconstituted saliva according to the invention is therefore useful for compensating for and repairing salivary deficiency and/or for maintaining more significant residual moisture in saliva-deficient mouths.

According to one aspect of the invention, the salivary substitute can be presented in liquid or gel form.

One formulation example can be provided by way of indication:
- egg-white powder: 0.5 g
- sorbitol: 1 g
- sodium bicarbonate: 0.5 g
- calcium carbonate: 0.5 g
- sodium fluoride : 0.025 mg
- Natrosol® 250 HX polymer: 0.5 g
- water: 100 ml
- aromas: sufficient quantity for neutralizing taste.

Preferably, the salivary substitute is packaged in the form of single doses of 2 to 5 ml, able to provide the suitable volume of salivary packing of a xerostomic mouth.

For the protection of the stability of the composition and the impermeability to oxygen and to radiation but also for the comfort of use by the patient, for an easy transport, it is possible preferably to run to "stick" packages. These packages, in the form of specific airtight cases, impermeable to light and oxygen, are produced from a flexible metalloplastic jacket. They ensure the physico-chemical stability of said substitute.

Advantageously, this packaging is easy to transport and makes possible an easy use of the salivary substitute at any moment of the day.

Regarding the plan of action, it is understood that the use of a salivary substitute that is analogous to natural saliva is very effective and achieves comfort for the individuals suffering from xerostomies.

The effect for one dose can extend for approximately one hour.

Thus, the use of one dose of salivary substitute according to the invention makes it possible for individuals who are suffering from xerostomies to talk easily or to take meals under good conditions, for example.

The invention claimed is:

1. A method of compensating for and repairing salivary deficiency in a subject in need thereof, consisting essentially of:
   administering a therapeutically effective amount of the salivary substitute to said subject,
   wherein the salivary substitute consists essentially of therapeutically effective amounts of:
   egg white powder, a polymer of high molecular weight selected from the group consisting of sodium carboxymethyl cellulose, hydroxyethyl cellulose, hydroxypropyl cellulose, hydroxypropyl methyl cellulose, carboxymethyl cellulose, guar gum, xanthan gum, gum Arabic, alginic acid, carboxy-vinyl polymers, carbomers, polyethylene glycol, gelatin, povidone, pectins, hyaluronic acid and combinations thereof, and a polyol selected from the group consisting of sorbitol and mannitol.

2. The method according to claim 1, wherein the salivary substitute has a viscosity between 1 and 5 poise.

3. A method of compensating for and repairing salivary deficiency in a subject in need thereof, consisting essentially of:

administering a therapeutically effective amount of the salivary substitute to said subject, wherein the salivary substitute consists essentially of therapeutically effective amounts of:

egg white powder, a polymer of high molecular weight selected from the group consisting of sodium carboxymethyl cellulose, hydroxyethyl cellulose, hydroxypropyl cellulose, hydroxypropyl methyl cellulose, carboxymethyl cellulose, guar gum, xanthan gum, gum Arabic, alginic acid, carboxy-vinyl polymers, carbomers, polyethylene glycol, gelatin, povidone, pectins, hyaluronic acid and combinations thereof, a substance to adjust pH selected from the group consisting of calcium carbonate and sodium carbonate, and a polyol selected from the group consisting of sorbitol and mannitol.

4. The method according to claim 3, wherein the salivary substitute has a viscosity between 1 and 5 poise.

5. The method according to claim 3, wherein the salivary substitute has a pH between 7.5 and 9.

\* \* \* \* \*